(12) United States Patent
Devereaux

(10) Patent No.: US 6,267,969 B1
(45) Date of Patent: Jul. 31, 2001

(54) UNIT-OF-USE REAGENT COMPOSITION FOR SPECIFIC BINDING ASSAYS

(75) Inventor: Sharon M. Devereaux, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/263,500

(22) Filed: Jun. 21, 1994

Related U.S. Application Data

(63) Continuation of application No. 07/776,518, filed on Oct. 11, 1991, now abandoned.

(51) Int. Cl.[7] ................................ A61K 9/00; A61K 9/48
(52) U.S. Cl. .................... 424/400; 424/451; 424/455; 424/457; 424/458; 424/464; 424/468; 424/473; 436/518
(58) Field of Search .................. 422/56, 57, 58; 435/7.1, 188, 969, 970, 963, 962, 7.9; 436/518, 523, 524, 528, 535, 18, 176, 826, 533, 534; 424/400, 451, 455, 457, 458, 464, 468, 473

(56) References Cited

U.S. PATENT DOCUMENTS

| | | | |
|---|---|---|---|
| 3,963,441 | | 6/1976 | Dietrich ........................ 23/253 R |
| 3,975,162 | * | 8/1976 | Renn .............................. 422/56 |
| 4,820,627 | * | 4/1989 | McGeehan ........................ 435/6 |
| 4,966,856 | * | 10/1990 | Ito et al. ...................... 436/170 |
| 5,009,994 | * | 4/1991 | McGeehan ........................ 435/4 |
| 5,102,788 | * | 4/1992 | Cole ............................. 436/525 |

FOREIGN PATENT DOCUMENTS 0062968 10/1982 (EP) ........................... G01N/33/50

* cited by examiner

Primary Examiner—Bennett Celsa
Assistant Examiner—P. Ponnaluri
(74) Attorney, Agent, or Firm—Regina M. Anderson; David L. Weinstein

(57) ABSTRACT

Unit-of-use reagent compositions and methods for preparing such reagent compositions are disclosed. The reagent composition comprises one or more reagents which are necessary for a specific binding assay and which are incorporated in a porous material which is encapsulated in a carrier matrix. The unit-of-use reagent composition can be lyophilized to avoid the need for cold storage of the reagent composition.

17 Claims, No Drawings

UNIT-OF-USE REAGENT COMPOSITION FOR SPECIFIC BINDING ASSAYS

This application is a continuation of U.S. application Ser. No. 07/776,518, filed Oct. 11, 1991 now abandoned.

BACKGROUND OF THE INVENTION

1. Field of the Invention

The invention relates generally to the field of assay reagents and their use in diagnostic assays. More particularly, the present invention relates to unit-of-use lyophilized reagent compositions, which are especially advantageous in diagnostic assays.

2. Description of Related Art

Various analytical procedures are commonly used in diagnostic assays to determine the presence and/or amount of substances of interest or clinical significance in test samples, such as body fluids. These clinically significant or interesting substances are commonly referred to as analytes. Diagnostic assays have become an indispensable means for detecting analytes in test samples by using the mutual reaction between the analyte and a specific binding member, as typified by the immunoreaction between an antigen and an antibody to that antigen.

Commercially available test devices for performing specific binding assays are usually in the form of test kits comprising packaged combinations of containers holding individual solutions of the reagents necessary for carrying out the assay. To perform the desired assay technique, aliquots of such reagent solutions must be manually or instrumentally dispensed into a reaction vessel with the test sample. If manually dispensed, the assay requires the time and skill of a technician, and if instrumentally dispensed, the assay requires the expense and maintenance of a dispensing apparatus.

Reagent impregnated solid phase test devices have been developed for specific binding assays to overcome the need for reagent measurements and the dispensing of individual reagents. Commonly used solid phase devices of this type include dipsticks, test strips, vials and flow-through devices wherein most or all of the necessary reagents are incorporated within the solid phase material. The assay reagents are generally applied to and dried upon the solid phase material to form reactive sites.

Dipstick devices generally involve a plastic strip with a reagent-containing matrix layered thereon. Typically, a test sample is applied to the device, and the presence of analyte is indicated by a reaction in the matrix layer between the analyte and assay reagent which produces a visually detectable signal such as color-formation. Hochstrasser (U.S. Pat. 4,059,407) discloses a dipstick device which is immersed in a biological fluid to detect analyte in the fluid. Also of interest in the area of dipstick devices are U.S. Pat. Nos. 3,802,842; 3,915,639 and 4,689,309 and WO Application No. 8,600,670.

Test strip devices are exemplified by the devices of Deutsch et al. which involve chromatographic test strips (U.S. Pat. Nos. 4,094,647, 4,235,601 and 4,361,537). The typical device comprises a material capable of transporting a solution by capillary action, i.e., wicking. Different areas or zones along the strip contain the assay reagents needed to produce a detectable signal upon the transport of analyte to or through such zones. The device is suited for both chemical assays and binding assays which are typified by the binding reaction between an antigen and complementary antibody. Many variations on the Deutsch device have been disclosed. Also of interest in the area of test strips are U.S. Pat. Nos. 4,168,146; 4,298,688; 4,435,504; 4,461,829; 4,517,288 and 4,740,468; European Patent Office Publication Nos. 88,636; 259,157; and 267,006; and German Patent No. 3,445,816.

Flow-through devices generally involve a porous material incorporated with an immobilized assay reagent. Test sample is applied to and flows through the porous material, and analyte in the sample reacts with the reagent to produce an immobilized complex that can then be detected on the porous material. Tom et al. (U.S. Pat. Nos. 4,366,241) disclose a bibulous material with an immunosorbing zone containing an immobilized analyte-specific antibody to which the test sample is directly applied. Other flow-through devices are described in U.S. Pat. Nos. 3,825,410; 3,888,629; 4,446,232; 4,587,102; 4,632,901; 4,637,978 and 4,727,019 and European Patent Office Publication Nos. 212,603; 217,403 and 249,851.

Previously known binding assay devices are generally considered difficult to manufacture. Typically, the reagents are applied individually to the solid phase to form reactive sites with drying of the solid phase after each addition, i.e., the manufacturer must supply the measuring and dispensing skills required by the assays. The dipstick, test strip and flow-through devices also are complicated because the chemical or physical reactions take place in the solid phase as the test sample passes through or migrates along the solid phase, and therefore, the solid phase must be designed to allow appropriate incubation and reaction times between each reactive site. In addition, when such devices are constructed they must be incorporated with the reagents specific for the analyte to be detected. This results in the need to change production techniques for each analyte of interest. Moreover, the reagents incorporated by direct application to and drying upon the solid phase a subject to changes in stability during the storage of the device.

SUMMARY OF THE INVENTION

The present invention involves reagent compositions for specific binding assays and methods for their preparation. One object of the present invention is to provide unit-of-use reagent compositions for specific binding assays. Another object of the present invention is to provide stable reagent compositions which can undergo storage conditions for extended periods of time. The novel reagent compositions of the present invention can be reacted with the test sample, and the resultant binding complexes of interest can be removed from the reaction mixture by any suitable separation means for subsequent detection. The novel unit-of-use reagent compositions obviate the need for measuring and dispensing individual assay reagents in the assay procedure. Moreover, the unit-of-use reagent compositions of the present invention have enhanced stability for long term storage.

The unit-of-use reagent composition for a specific binding assay contains at least one assay reagent, wherein the reagent includes a specific binding member in an amount sufficient to perform a single binding assay, and a porous material. The assay reagent is incorporated within the porous material, and the porous material is then coated or encapsulated with a carrier matrix. The carrier matrix is then dried thereby stabilizing the assay reagent. The carrier matrix can be reconstituted upon contact with a solvent, thereby releasing the assay reagent from the porous material. The moldable carrier matrix is typically a gelatin, such as, a calf skin gelatin, fish gelatin, swine skin gelatin or a vegetable gelatin.

The present invention also relates to a method of forming a unit-of-use reagent composition for a specific binding assay. In the method, an assay reagent is combined with a carrier matrix solution thereby forming a mixture. An aliquot of the mixture is applied to a porous material and cooled or allowed to dry. The porous material is then lyophilized. Upon contact with an appropriate solvent, such as a test sample, the composition rehydrates to expose the assay reagent for a specific binding reaction.

DETAILED DESCRIPTION OF THE INVENTION

The present invention involves a unit-of-use reagent composition and methods for preparing the composition. The reagent composition can be stored for prolonged periods at room temperature and can be dispensed by a technician without the need for multiple reagent measurements and additions to the reaction vessel or test device.

Before proceeding further with the description of the various embodiments of the present invention, a number of terms will be defined. A variety of assay techniques in which the unit-of-use reagent composition of the present invention can be used are also described.

I. Definitions

The term "specific binding member", as used herein, refers to a member of a specific binding pair, i.e., two different molecules where one of the molecules through chemical or physical means specifically binds to the second molecule. In addition to antigen and antibody-specific binding pairs, other specific binding pairs include biotin and avidin, carbohydrates and lectins, complementary nucleotide sequences (including probe and capture nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

Immunoreactive specific binding members include antigens, haptens, antibodies, and portions or complexes thereof, including those formed by recombinant DNA methods, fragmentation methods or peptide synthesis. Typically, the immunoreactive specific binding member is capable of binding either to the analyte as in a sandwich assay, to the capture reagent as in a competitive assay, or to an ancillary specific binding member as in an indirect assay. If an antibody is used, it can be a monoclonal antibody, polyclonal antibody, antibody fragment, recombinant antibody, a mixture thereof, or a mixture of an antibody and other specific binding members. The details of the preparation of such antibodies and their suitability for use as specific binding members are well known to those skilled in the art.

The term "analyte", as used herein, refers to the substance of interest in the test sample to be detected or measured in the assay. The analyte can be any substance for which there exists a naturally occurring specific binding member (e.g., an antibody) or for which a specific binding member can be prepared. The analyte may be bound to one or more specific binding members in the assay. "Analyte" also includes any antigenic substances, haptens, antibodies, and combinations thereof. Analytes of interest include, but are not limited to, proteins, peptides, amino acids, hormones, steroids, vitamins, drugs including those administered for therapeutic purposes as well as those administered for illicit purposes, a bacterium, a virus, and metabolites of or antibodies to any of the above substances.

The term "indicator reagent", as used herein, refers to a detectable label directly or indirectly attached to a specific binding member. The label can be attached to the specific binding member prior to the assay or during the performance of the assay. The indicator reagent produces a detectable signal that is related to the presence or amount of analyte in the test sample. In general, the indicator reagent is detected or measured after it is captured on a solid phase material, but unbound indicator reagent may also be detected or measured to determine the result of an assay. The specific binding member of the indicator reagent can be a member of any specific binding pair including immunoreactants. The label of the indicator reagent is capable of producing a signal detectable by visual or instrumental means. A variety of different indicator reagents can be formed by varying either the label or the specific binding member.

The term "label", as used herein, refers to any substance which is or becomes attached to a specific binding member and which is capable of producing a signal that is detectable by visual or instrumental means. Such labels include, but are not limited to, chromogens; catalysts; fluorescent compounds; chemiluminescent compounds; radioactive labels; direct visual labels including colloidal metallic, non-metallic particles, dye particles, enzymes or substrates, or organic polymer latex particles; liposomes or other vesicles containing signal producing substances; and the like. The selection of a particular label is not critical to the present invention, but the label will be capable of generating a detectable signal either by itself or in conjunction with one or more additional substances as in an enzyme/substrate signal producing system.

The term "signal producing system", as used herein, refers to the group of assay reagents that are needed to produce the desired reaction product or signal. For example, one or more signal producing components can be used to react with a label and generate the detectable signal, e.g., when the label is an enzyme, amplification of the detectable signal is obtained by the enzyme reacting with one or more substrates or additional enzymes to produce a detectable reaction product. "Detectable signal" as used herein, is intended in its broadest sense to include any observable change in a system parameter, such as a change in or appearance of a reactant, an observable precipitation of any component in the test sample or a change in any other parameter whether detected by direct visual observation or instrumental means.

The term "capture reagent", as used herein, refers to a specific binding member which may be specific either for the analyte as in a sandwich assay, for the indicator reagent and analyte as in a competitive assay, or for an ancillary specific binding member which itself is specific for the analyte as in an indirect assay. Thus, the specific binding member can be any molecule capable of specifically binding with another, just as in the indicator reagent specific binding members. In a solid phase assay, the capture reagent is directly or indirectly attached to a substantially solid material. The solid phase facilitates the separation of the analyte and/or assay reagents or complexes thereof to be separated from the test solution. Typically, the attachment of the specific binding member to the solid phase material is substantially irreversible and can include covalent or non-covalent mechanisms. The capture reagent can be directly attached to the solid phase particle by adsorption, but preferably the capture reagent is indirectly attached to the particle with a cross-linking agent. The cross-linking agent is preferably selected from glutaraldehyde, formaldehyde, glyoxal, acrolein and acetaldehyde. It is most preferable that the capture reagent be covalently bonded to the particles by a sensitization procedure using glutaraldehyde.

The term "ancillary specific binding member", as used herein, refers to any member of a specific binding pair which is used in the assay in addition to the specific binding members of the capture reagent and the indicator reagent to detect the presence or amount of the analyte in the test sample. One or more ancillary specific binding members can be used in an assay. For example, an ancillary specific binding member can be capable of binding the analyte, as well as a second specific binding member to which the analyte itself could not attach.

II. Diagnostic Assays

The novel unit-of-use reagent compositions of the present invention are advantageously used in a variety of immunoassay formats. The present invention, however, is not limited to immunoassays. Any assay configuration using specific binding members and a detectable label can be performed using the unit-of-use reagent compositions, but immunoassay formats will be described herein to simplify the disclosure.

Binding assays are generally categorized into one of two major classes, homogeneous and heterogeneous assays. In a homogeneous assay, the analyte and assay reagents form a test solution and are not separated prior to the detection of the signal produced by the indicator reagent. In a heterogeneous assay, either a solid phase material is used which allows the separation of bound from unbound reaction components, or a reagent of the initial solution is caused to precipitate and is subsequently removed from the test solution. These assays may be further divided into sandwich and competitive assays, and variations thereof.

Schematic representations of examples of several such types of assays for both antigen and antibody analytes follow. It will be appreciated, however, that one skilled in the art can conceive of many other types of assays, including assays for analytes other than antigens or antibodies, to which the present inventive concepts can be applied.

Heterogeneous Assays

1. Direct Assay

| Solid Phase:Capture Reagent | Analyte | Indicator Reagent |
| --- | --- | --- |
| . - Ab particle:antibody | Ag Antigen | Ab* labeled antibody |

The specific binding member of the indicator reagent may or may not be the same specific binding member as the capture reagent. Antigen and antibody analytes are determinable using the foregoing reaction scheme. Variations on the reaction scheme include the following, without limitation:

| Solid Phase:Capture Reagent | Analyte | Indicator Reagent |
| --- | --- | --- |
| . - Ag particle:antigen | Ab Antibody | Ab* labeled anti-antibody |
| . - Ag particle:antigen | Ab Antibody | Ag* labeled antigen |
| . - Ab - Ag particle:antibody:antigen | Ab Antibody | Ab* labeled anti-antibody |

2. Indirect Assay

In this group of assays, an additional specific binding member is used together with those of the indicator and capture reagents to form the detectable binding complex. For example, an ancillary specific binding member can be used where the indicator reagent specifically binds with the ancillary specific binding member which in turn binds to the analyte. It is also desirable, in some cases, to capture the analyte directly on the solid phase.

| Solid Phase:Capture Reagent | Analyte | Ancillary | Indicator Reagent |
| --- | --- | --- | --- |
| . - Ab particle:antibody | Ag Antigen | Ab antibody | Ab* labeled anti-antibody |
| . particle | Ag Antigen | Ab antibody | Ab* labeled anti-antibody |

3. Competitive Assay

Examples of competitive assay formats include the following:

| Solid Phase:Capture Reagent | Analyte | Indicator Reagent |
| --- | --- | --- |
| . - Ab particle:antibody | Ag Antigen | Ag* labeled antigen |
| . - Ag particle:antigen | Ab Antibody | Ab* labeled antibody |

In these examples, both the analyte in the test sample and the specific binding member of the indicator reagent are capable of competitively binding to the capture reagent. The amount of indicator reagent so bound reflects the amount of analyte in the test sample. Ancillary specific binding members can also be used in competitive assays. Generalized examples describing sandwich and competitive assays which can employ the reagent compositions of the present invention are set forth below. Detailed discussions of sandwich assay procedures using the reagent composition of the invention are set forth in the examples which follow.

A solid phase sandwich assay uses a capture reagent, i.e., specific binding member, attached to a solid phase material. The capture reagent is contacted with a test sample, suspected of containing the analyte, and an indicator reagent comprising a second specific binding member that has been labeled. The reagents and test sample can be contacted simultaneously or sequentially, either singly or in combination. A binding reaction results in the formation of a capture reagent/analyte/indicator reagent complex immobilized upon the solid phase material. The assay can also comprise the step of separating the resultant complex from the excess reagents and test sample. The complex retained on the solid phase material is detected by examining the solid phase for the indicator reagent. If analyte is present in the sample, then label will be present on the solid phase material. The amount of label on the solid phase is a function of the amount of analyte in the sample.

The reagent compositions of the present invention are advantageously used in the sandwich assay formats, including the forward, reverse and simultaneous techniques. Typically, a forward assay involves the contact of the test sample to the capture reagent followed by a certain incubation period which is in turn followed by the addition of the indicator reagent. A reverse assay involves the addition of the indicator reagent to the test sample followed by the addition of the capture reagent after a certain incubation period. A simultaneous assay involves a single incubation step as the capture reagent and indicator reagent are both contacted to the test sample at the same time, such as when both the capture reagent and indicator reagent are encapsulated in a carrier matrix in a reagent composition of the present invention.

In addition, the present invention can be used in an indirect sandwich assay with the formation of a complex of capture reagent/analyte/analyte-specific binding member/indicator reagent. In this case, the additional analyte-specific binding member is an ancillary specific binding member which can be added separately or included in the encapsulated reagent composition.

The reagent compositions of the present invention can also be used in a competitive assay. In a solid phase competitive configuration, the capture reagent is again attached to a solid phase material and is contacted with both test sample and an indicator reagent. The indicator reagent is formed from an analyte or analyte-analog which has been labeled. A binding reaction occurs and results in the formation of complexes of (1) solid phase:capture reagent/analyte complex and (2) solid phase:capture reagent/indicator reagent complex. In the competitive assay, the amount of label on the solid phase is inversely related to the amount of analyte in the sample. Thus, a positive test sample will generate a decrease in signal. For example, in a theophylline assay, an anti-theophylline antibody (either monoclonal or polyclonal capture reagent) can be immobilized upon a solid support. A competition for binding to that antibody can be established between an indicator reagent of labeled theophylline and unlabeled theophylline present in the test sample. The immunoreaction results in a solid phase:capture reagent/indicator reagent complex if theophylline, or a threshold amount of theophylline, is not present in the test sample. Increased theophylline levels in the test sample will result in decreased indicator reagent associated with the solid phase.

Homogeneous Assays

Homogeneous assays do not require the separation of the test solution and the indicator reagent prior to observation of the indicator reagent. This broad classification includes many formats such as those described below as well as others apparent to one skilled in the art using the novel reagent compositions of the present invention.

A major category of homogeneous assays are the agglutination assays which can also be performed using the reagent compositions of the present invention. Agglutination reactions and their procedures are generally well known in the art. A typical agglutination reaction consists of the clumping together of analyte in the presence of an analyte-specific binding member. This clumping or agglutination of reaction components is monitored to determine the presence or amount of the analyte sought to be detected. The agglutination reaction can be monitored by labeling a reaction component, e.g., a specific binding member, and detecting the signal associated with either the agglutinated or the unagglutinated reagents. Detection can be achieved visually by observing the clumping of the reaction medium, by the settling or pelleting of the indicator reagent in a gravitational field, by changes in light scattering, or by changes in the spectral properties of the indicator reagent.

1. Direct Assay

In a direct agglutination assay, if a polyvalent analyte is present, two or more labeled specific binding members can bind to the analyte, thereby causing the indicator reagent and analyte to aggregate. An increase in the aggregation can indicate an increase in the amount of analyte present in the test sample. The capture reagent-coated particle can also serve as the detectable label. For example, the reagent-coated particle can be a colored particle which facilitates the detection of particle agglomerates in agglutination assays.

2. Indirect/Competitive Assay

An indirect agglutination assay can be constructed using an ancillary binding member that competes with the analyte for binding to the indicator reagent. Such an assay configuration is especially useful for the analysis of a monovalent analyte. In this assay, more than one ancillary binding member is attached to an insoluble material and is contacted to the indicator reagent and test sample. If the analyte is absent, or below a threshold level, then agglutination occurs due to the binding of more than one indicator reagent to the insoluble material. If the analyte is present in the test sample, then the analyte competitively binds to the indicator reagent, thereby blocking the indicator reagent's binding to the insoluble material, and the presence of the analyte is indicated by a decrease in agglutination of the indicator reagent.

III. Lyphilized Reagent Compositions

The present invention involves the encapsulation of a capture reagent-coated particle or particles in a carrier matrix which is advantageously used to dispense the reagent composition in the amount needed for a single assay. Preferably, the carrier matrix material and the encapsulated reagents can be lyophilized. The lyophilized reagent composition is rehydrated during the performance of the diagnostic assay, thereby allowing the assay reagent or reagents to be released. The assay reagents can be included in the unit of use reagent composition to produce various detection or measurement formats including sandwich assays, competitive assays and agglutination assays in which all or most of the reagents necessary for the assay are preferably contained by the carrier matrix. The lyophilization of the reagent composition is not critical to the present invention, but it has been found to extend reagent stability and facilitate the handling and packaging of the reagent compositions. The novel reagent compositions can be used in diagnostic instruments in place of multiple liquid reagents, or they may be used with manual assay devices enabling a single addition of assay reagents by the user without the need for reagent measurements.

The carrier matrix can comprise any substance capable of being incorporated with one or more specific binding assay reagents. In one embodiment, the carrier matrix is a moldable material which enables the use of individual mold cavities for the formation of separate molded units which contain aliquots of reagents sufficient for a single assay. Alternatively, the carrier matrix enables the formation of sheets or similar masses that can be removed from a single mold cavity which may then be divided or separated into unit-of-use blocks or plugs. In either case, the units can then be lyophilized with the resultant formation of a dried reagent composition with high structural integrity. In yet another embodiment, the carrier matrix may be used to coat or embed an appropriate amount of assay reagent on a bibulous material which is part of an assay device. For example, an indicator reagent in a carrier matrix may be applied to a porous filter, thereby encasing the reagent. The addition of a liquid test sample to the porous filter will release the assay reagent from the carrier matrix for reaction with the test sample or other assay reagents. In yet another embodiment, the assay reagent so released may also migrate from the bibulous material to another portion of the assay device.

Suitable materials for the carrier matrix are selected from substances which will rehydrate with the addition of a test sample, or other appropriate solvent, but which will be inert with respect to the assay reagents and which can be dried or lyophilized. Most preferably, the carrier matrix will rapidly rehydrate and dissolve when contacted with the solvent, thereby releasing any assay reagents contained therein. The dissolved carrier matrix can be then be washed away at the end of the assay's incubation period.

Gelatin was found to be the most preferred carrier matrix material. Gelatin sources include calf skin gelatin and swine skin gelatin of various Blooms (i.e., Bloom number is an indication of the strength of the gels produced, wherein the higher the Bloom number the stronger the gel.) Fish gelatin and vegetable gelatins can also be used. Assay reagents are easily mixed with gelatin solutions, and the cooled gelatin forms a gelled mass which is readily moldable. The units of gelatin encapsulated reagent compositions can be lyophilized with the resultant formation of a dried protein with high structural integrity. The lyophilized gelatin will rapidly rehydrate and dissolve when contacted with a solvent, releasing any reagents contained therein, and the gelatin can be washed away.

The test sample can be derived from any source, such as a physiological fluid, including, blood, saliva, ocular lens fluid, cerebral spinal fluid, sweat, urine, milk, ascites fluid, mucous, synovial fluid, peritoneal fluid, amniotic fluid or the like. The fluid can be pretreated prior to use, such as preparing plasma from blood, diluting viscous fluids, or the like; methods of treatment can involve filtration, distillation, concentration, inactivation of interfering components, and the addition of reagents such as additional solvents. Besides physiological fluids, other liquid samples can be used such as water, food products and the like. In addition, a solid can be used once the sample material is modified to form a liquid medium.

In one embodiment of the present invention, the capture reagent is attached to a plurality of particles, e.g., microparticles, which serve as the solid phase material. The particles can be selected by one skilled in the art from any suitable type of particulate material including, but not limited to, those composed of polystyrene, polyacrylamide, polyurethane, polymethylacrylate, polypropylene, polytetrafluoroethylene, polyacrylonitrile, polycarbonate or similar materials. In one embodiment, the particles may be made of or contain a magnetic or magnetizable material whereby the particles can be removed from from a reaction mixture by the application of a magnetic field.

The capture reagent-coated particles are encapsulated in the carrier matrix which can then be lyophilized. The lyophilized reagent composition is reconstituted during the performance of the assay, and the carrier matrix releases the capture reagent-coated particles for reaction with the analyte and indicator reagent. The particles can then be separated from the test solution. For example, the particles may be separated from the test solution by centrifugation, precipitation, agglutination, the application of a magnetic field, filtration or entrapment by means of an additional solid phase base material. A suitable solid phase base material can be any porous, absorbant or bibulous material which can separate the particles from the test solution for observation. Preferable solid phase base materials include fiberglass, cellulose or nylon pads through which the test solution and unbound reagents will pass. The size of the particles is not critical, although it is preferred that the average diameter be smaller than the average pore size of the solid phase base material.

In an alternative embodiment, the capture reagent is immobilized upon a single particle, such as a quarter-inch bead. In this instance the assay can be performed in a reaction vessel such as a cuvette, microtitre plate, or glass or plastic test tube, from which the test solution, unbound reagents and wash solutions can be removed.

In another embodiment of the present invention, the indicator reagent as well as the capture reagent-coated particle is encapsulated in the carrier matrix. The inclusion of a sugar additive has been found to protect the indicator reagent during the lyophilization process and to enhance the stability characteristics of the indicator reagent's label component. For example, d-trehalose dihydrate was found to provide the best stabilizing response for enzyme labels. Other sugars which may be advantageously used in the production of the reagent compositions of the present invention include dextran, lactose, sucrose, maltose, xylose, arabitol and xylitol. Preferably, the sugar additive is present in the final composition at a concentration of from about 0.1% to about 50%. Most preferably, the sugar additive is present at a concentration of from about 0.1% to about 20%.

As described above, different molds can be used to form the desired carrier matrix unit. Although not a necessity, the mold can be pretreated with a release agent to facilitate the removal of the newly formed reagent composition units. Pretreatment of the molds in the present invention was typically performed by coating or lightly spraying the surface of the mold with lecithin.

The unit of use reagent compositions may be air dried or lyophilized. The details of different lyophilization procedures are well known to those skilled in the art. In general, the material to be lyophilized should be brought below the eutectic temperature of this material prior to application of vacuum. For aqueous materials, a temperature of less than $-40°$ F. will ensure adequate freezing. This can be accomplished by application of the device to dry ice, immersion of the device into a dry ice-acetone bath or application of the device to freezing surfaces available in many commercial freeze-drying devices. The vacuum applied to the material should be sufficient to ensure removal of water by sublimation.

EXAMPLES

The following Examples illustrate how to make the novel reagent compositions of the present invention and how to perform assay procedures using those reagent compositions. The Examples, however, are intended only to be illustrative, and are not to be construed as placing limitations upon the scope of the invention, which scope is defined solely by the appended claims.

Example 1

Preparation of a Lyophilized Reagent Composition for a Carcinoembryonic Antigen (CEA) Enzyme Immunoassay a) Preparation of the Assay Reagents Ten grams of d-trehalose dihydrate (Aldrich, Milwaukee, Wis.) and two grams of calf skin gelatin (60 Bloom, Sigma, St. Louis, Mo.) were combined in distilled water (approximately 10 ml) in a 50 milliliter graduated plastic centrifuge tube. The volume was brought to approximately 30 milliliters with distilled water, and the mixture was blended by vortexing. The mixture was heated by placing the tube in a beaker of water situated on a hot plate. The water was brought to a boil. The tube was removed, and the volume of solution was brought to 50 milliliters with distilled water and further mixing. The resultant 4% gelatin, 20% trehalose solution was later mixed one part by volume for each one part of test reagent.

Capture reagent-coated particles comprised a microparticle solid phase of cyanogen bromide-activated Sepharose® 4B (Sigma) coated with anti-CEA mouse monoclonal antibody (2 mg/ml). The capture reagent-coated particles were suspended 5% in a specimen diluent buffer [SDB; Tris (hydroxymethyl)aminomethane buffer (Tris) containing gentamicin as a preservative] The indicator reagent was a conjugate of anti-CEA antibody (mouse monoclonal) and horseradish peroxidase (HRPO) (150 ng/ml).

A reagent mixture was formed by combining equal volumes of the suspended capture reagent-coated particles and the indicator reagent (100 µl of indicator reagent for each 100 µl of capture reagent-coated particles in SDB). The reagent mixture was then combined with an equal volume of the carrier matrix solution (200 µl of gelatin solution for each 100 µl of indicator reagent and 100 µl of capture reagent-coated particles in SDB) to form the reagent composition.

b) Lyophilization of the Reagent Composition

The carrier matrix mold was a ¼" thick plastic plate with individual ⅜" cavities. The mold was lightly sprayed with lecithin to facilitate the removal of the reagent composition units.

An aliquot of the reagent composition (400 µl) was dispensed into each mold cavity using a precision pipette. The mold was exposed to −70° C. in a freezer for approximately three hours. The molds were then transferred to −50° C. freezer shelves where they were kept under a vacuum for 3.5 hours. The shelf temperature was then increased to −35° C. and maintained for 16 hours. The lyophilization cycle was completed by sublimation at a shelf temperature of −10° C. for five hours, followed by a shelf temperature of +30° C. for about 18 hours. The lyophilized reagent composition units were removed from the mold and stored in glass vials with silica gel desiccant. Storage at 4° C. ensured extended stability. Reagent compositions stored at room temperature, however, exhibited stable performance with little change in performance from those reagent compositions stored at 4° C., and better performance than liquid reagent control compositions.

c) Acceptability of the Lyophilized Reagent Composition in the CEA Assay

A unit of the lyophilized reagent composition was placed in a filtered reaction vessel that could be maintained at a temperature of 40° C. and rotated during incubation to enhance assay kinetics. The lyophilized reagent composition was combined with a test sample or CEA assay standard solution in the reaction vessel. The CEA standards included samples of 0, 4, 24, 44 and 84 nanograms of antigen per milliliter of Tris buffer. The test samples, or standards, and the lyophilized reagent composition were incubated at 40° C., while rotating, for 20 minutes. If CEA was present, then a capture reagent/antigen/indicator reagent complex was formed during the incubation period. After incubation, the unbound indicator reagent was washed from the reaction vessel with 0.9% sodium chloride solution or phosphate buffered saline solution; a three milliliter volume of wash solution was drawn through the reaction vessel, and this process was repeated nine times.

The performance of the reagent composition was measured by detecting the amount of capture reagent/antigen/indicator reagent complex formed during incubation. The more antigen present in the test sample, the more ternary complex was formed, and therefore, the greater the amount of indicator reagent held in the reaction vessel. Tetramethylbenzidine (TMB) was used as the color-producing substrate with which the HRPO of the indicator reagent would react. Three hundred microliters of TMB substrate was dispensed into each reaction vessel. The reaction vessels were incubated for eight minutes at 40° C. while rotating. A blue color was generated in the presence of HRPO, i.e., in those samples which had formed a capture reagent/antigen/indicator reagent complex. Color development was quenched with the addition of sulfuric acid (1 ml, 1 N $H_2SO_4$), and the color development was read using a spectrophotometer (450 nm). Color measurements demonstrated that as the amount of analyte in the test sample increased, the amount of indicator reagent bound to the capture reagent also increased as shown by an increase in light absorbance. It was found that the detectable signal for both lyophilized reagent compositions and unlyophilized reagents was substantially the same, indicating that no substantial changes to the reagents occurred during the lyophilization process.

Example 2

Lyophilized Reagent Composition

A lyophilized reagent composition was prepared substantially in accordance with the protocol of Example 1, above, with the exception that a single polystyrene bead was used in lieu of the microparticles. The molded reagent compositions were formed by dispensing a single capture reagent-coated polystyrene bead into each mold cavity, followed by the addition of the indicator reagent and the gelatin solution. A CEA assay was performed substantially in accordance with the protocol of Example 1, and similar results were obtained.

The assay results are presented in Table 1 which compares the CEA concentration in the samples to the amount of color developed. The results demonstrated that as the amount of analyte in the test sample increased, the amount of indicator reagent bound to the capture reagent-coated bead also increased as shown by an increase in light absorbance.

TABLE 1

| | Polystyrene Bead Solid Phase | | | | |
|---|---|---|---|---|---|
| Standard | [CEA] ng/ml | ΔÅ450 | Average | S.D. | C.V. |
| 1 | 0 | 0.088 0.095 | 0.092 | 0.005 | 5.4% |
| 2 | 4 | 0.366 0.333 | 0.350 | 0.023 | 6.7% |
| 3 | 10 | 0.701 0.694 | 0.698 | 0.005 | 0.7% |
| 4 | 30 | 1.378 1.488 | 1.433 | 0.078 | 5.4% |
| 5 | 60 | 1.815 1.841 | 1.828 | 0.018 | 1.0% |

Example 3

Preparation of a Lyophilized Reagent Composition for a Human Chorionic Gonadotropin (hCG) Enzyme Immunoassay a) Preparation of the Assay Reagents One hundred microliters of conjugate (anti-hCG antibody/m-maleimidobenzoyl-N-hydroxysuccinimide ester) was mixed with an equal volume of matrix solution containing 0.5% gelatin and 6% sucrose made substantially in accordance with the process described in Example 1a, above.

b) Lyphilization of the Reagent Composition

An aliquot of the reagent composition (400 µl) was dispensed onto a porous filter material using a precision pipette. The filter was exposed to −70° C. in a freezer for two hours. The units were then transferred to −44° C. freezer shelves where they were kept under a vacuum for one hour. The shelf temperature was then increased to −20° C. and maintained for approximately two hours. The lyophilization cycle was completed by sublimation at a shelf temperature of 0° C. for approximately twelve hours, followed by a shelf temperature of +30° C. for about one hour. The lyophilized reagent composition units were removed from the mold and stored at room temperature in glass vials with silica gel desiccant.

c) Acceptability of the Lyophilized Reagent Composition in the hCG Assay

An hCG assay standard solution was contacted to the lyophilized reagent composition which overlaid a porous pad containing immobilized anti-hCG antibody. The hCG standards included samples of 0 and 100 nanograms of antigen per milliliter of Tris buffer. The test samples, or standards, and the assay reagents were incubated for 90 seconds. The incubation was followed by the removal of the lyophilized reagent composition filter and the washing of the porous pad. A chromagen solution of either 5-bromo-4-chloro-3-indolyl phosphate (0.5 mg/ml in Tris buffer) or nitro blue tetrazolium (0.2 mg/ml in Tris buffer) was then contacted to the porous pad. If hCG was present, then a capture reagent/antigen/indicator reagent complex was formed during the incubation period, and the addition of the chromagen resulted in the production of a visually detectable colored reaction product.

Example 4

Lyophilized Reagent Composition Stability a) Preparation of the Assay Reagents

A matrix solution was prepared substantially in accordance with the procedure described in Example 1 a, above. Anti-hCG antibody/alkaline phosphate conjugate (200 ml) was combined with gelatin (2.3 ml), dextran (4 g) and sucrose (4 g).

b) Lyophilization of the Reagent Composition

The lyophilized reagent composition units were prepared substantially in accordance with the procedure described in Example 3b, above. The units were subjected to heat stress conditions of 45° C. for a total of 111 days.

c) Acceptability of the Lyophilized Reagent Composition in the hCG Assay

Assays were performed, using the lyophilized reagent composition units, substantially in accordance with the procedure described in Example 3c, above. The results of assays performed throughout the stress period (days 3, 7, 17, 21, 28 and 111) provided identical results with the production of a visually detectable signal in the presence of analyte.

The concepts of the present invention are applicable to various types of binding assays. It will be appreciated, however, that one skilled in the art can conceive of other assays, including assays for analytes other than antigens or antibodies, to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as previously described and as set forth in the following claims.

What is claimed is:

1. An article comprising a unit-of-use reagent composition for a specific binding assay, said article comprising:
   a) a porous material;
   b) a mixture of an assay reagent and a carrier matrix, said mixture comprising gelatin, said assay reagent encapsulated by said carrier matrix, said mixture being coated onto said porous material, wherein said assay reagent is a specific binding member in an amount sufficient to perform a single binding assay; and
   wherein said carrier matrix is lyophilizable, and
   wherein said carrier matrix can be rehydrated upon contact with a solvent to expose or release said assay reagent from said porous material for a specific binding reaction.

2. The article according to claim 1, wherein said assay reagent is an indicator reagent specific for a substance selected from the group consisting of an analyte as in a sandwich assay, a capture reagent as in a competitive assay, and an ancillary specific binding member as in an indirect assay.

3. The article according to claim 1, wherein said gelatin is selected from the group consisting of calf skin gelatin, fish gelatin, swine skin gelatin, and vegetable gelatins.

4. The article according to claim 1, wherein said carrier matrix can be rehydrated upon contact with a test sample.

5. The article according to claim 1, further consisting essentially of an additional stabilizer for said assay reagent.

6. The article according to claim 5, wherein said stabilizer is a sugar.

7. The article according to claim 6, wherein said sugar is present at a concentration of from about 0.1% to about 50%.

8. The article according to claim 6, wherein said sugar is selected from the group consisting of trehalose, dextran, lactose, maltose, xylose, arabitol, xylitol, and sucrose.

9. The article according to claim 2, wherein said indicator reagent is selected from the group consisting of chromogens; catalysts; fluorescent compounds; chemiluminescent compounds; radioactive labels; direct visual labels including colloidal metallic, non-metallic particles, dye particles, and organic polymer latex particles; enzymes and substrates; and liposomes and other vesicles containing signal producing substances.

10. A method of forming an article comprising a unit-of-use reagent composition for a specific binding assay, said method comprising the steps of:
   a) combining an assay reagent with a solution comprising a carrier matrix, thereby forming a mixture, said mixture comprising gelatin, wherein said assay reagent comprises a specific binding member in an amount sufficient to perform a single binding assay;
   b) applying an aliquot of said mixture onto a porous material;
   c) allowing said porous material and said mixture applied thereon to dry to form said article comprising said unit-of-use reagent composition, said assay reagent encapsulated by said carrier matrix; and
   d) lyophilizing said article comprising said unit-of-use reagent composition, wherein said article can be rehydrated upon contact with a solvent, thereby exposing said assay reagent for a specific binding reaction.

11. The method according to claim 10, wherein said gelatin is selected from the group consisting of calf skin gelatin, fish gelatin, swine skin gelatin, and vegetable gelatins.

12. The method according to claim 10, further comprising the step of combining a stabilizer with said assay reagent.

13. The method according to claim 12, wherein said stabilizer is a sugar.

14. The method according to claim 13, wherein said sugar is present at a concentration of from about 0.1% to about 50%.

15. The method according to claim 13, wherein said sugar is selected from the group consisting of trehalose, dextran, lactose, maltose, xylose, arabitol, xylitol, and sucrose.

16. The method according to claim 10, wherein said assay reagent is an indicator reagent comprising a specific binding member conjugated to a label.

17. The method according to claim 16, wherein said label is selected from the group consisting of chromogens; catalysts; fluorescent compounds; chemiluminescent compounds; radioactive labels; direct visual labels including colloidal metallic, non-metallic articles, dye particles, and organic polymer latex particles; enzymes and substrates; and liposomes and other vesicles containing signal producing substances.

* * * * *

UNITED STATES PATENT AND TRADEMARK OFFICE
CERTIFICATE OF CORRECTION

PATENT NO.    : 6,267,969 B1
DATED         : July 31, 2001
INVENTOR(S)   : Sharon M. Devereaux It is certified that error appears in the above-identified patent and that said Letters Patent is hereby corrected as shown below:

<u>Column 16,</u>
Line 3, replace "colloidal metallic, non-metallic articles," with -- colloidal metallic, non-metallic particles, --.

Signed and Sealed this

Twenty-sixth Day of February, 2002

Attest:

JAMES E. ROGAN
Attesting Officer     Director of the United States Patent and Trademark Office